US00PP24695P3

(12) United States Plant Patent
Olesen

(10) Patent No.: US PP24,695 P3
(45) Date of Patent: Jul. 29, 2014

(54) CLIMBING ROSE PLANT NAMED 'POULCY014'

(50) Latin Name: ***Rosa* hybrid**
Varietal Denomination: Poulcy014

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 13/507,036

(22) Filed: May 31, 2012

(65) Prior Publication Data

US 2013/0326744 P1 Dec. 5, 2013

(51) Int. Cl.
*A01H 5/00* (2006.01)

(52) U.S. Cl.
USPC ..... Plt./115; Plt./101; Plt./109

(58) Field of Classification Search
USPC ..... Plt./101, 109, 115
See application file for complete search history.

*Primary Examiner* — Susan McCormick Ewoldt

(57) ABSTRACT

A new garden rose plant of the climbing class which has abundant, red flowers and attractive foliage. This new and distinct variety has shown to be uniform and stable in the resulting generations from asexual propagation.

3 Drawing Sheets

Botanical designation: *Rosa* hybrid.
Variety denomination: 'Poulcy014'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2001 and the resulting seeds were planted in a controlled environment in Fredensborg, Denmark. The new variety, named 'Poulcy014', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy014' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poulcy014' was selected in the spring of 2002 by the inventor as a single plant from the progeny of the aforementioned hybridization.

Asexual reproduction of 'Poulcy014' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poulcy014' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcy014' from a plant 2 years of age.

Specifically illustrated in FIG. 1 are open flowers and detached flower petals, FIG. 2 are flowers at various stages of development on a flowering branch, FIG. 3 are leaves an stems.

DETAILED DESCRIPTION OF THE VARIETY

Figure 1:
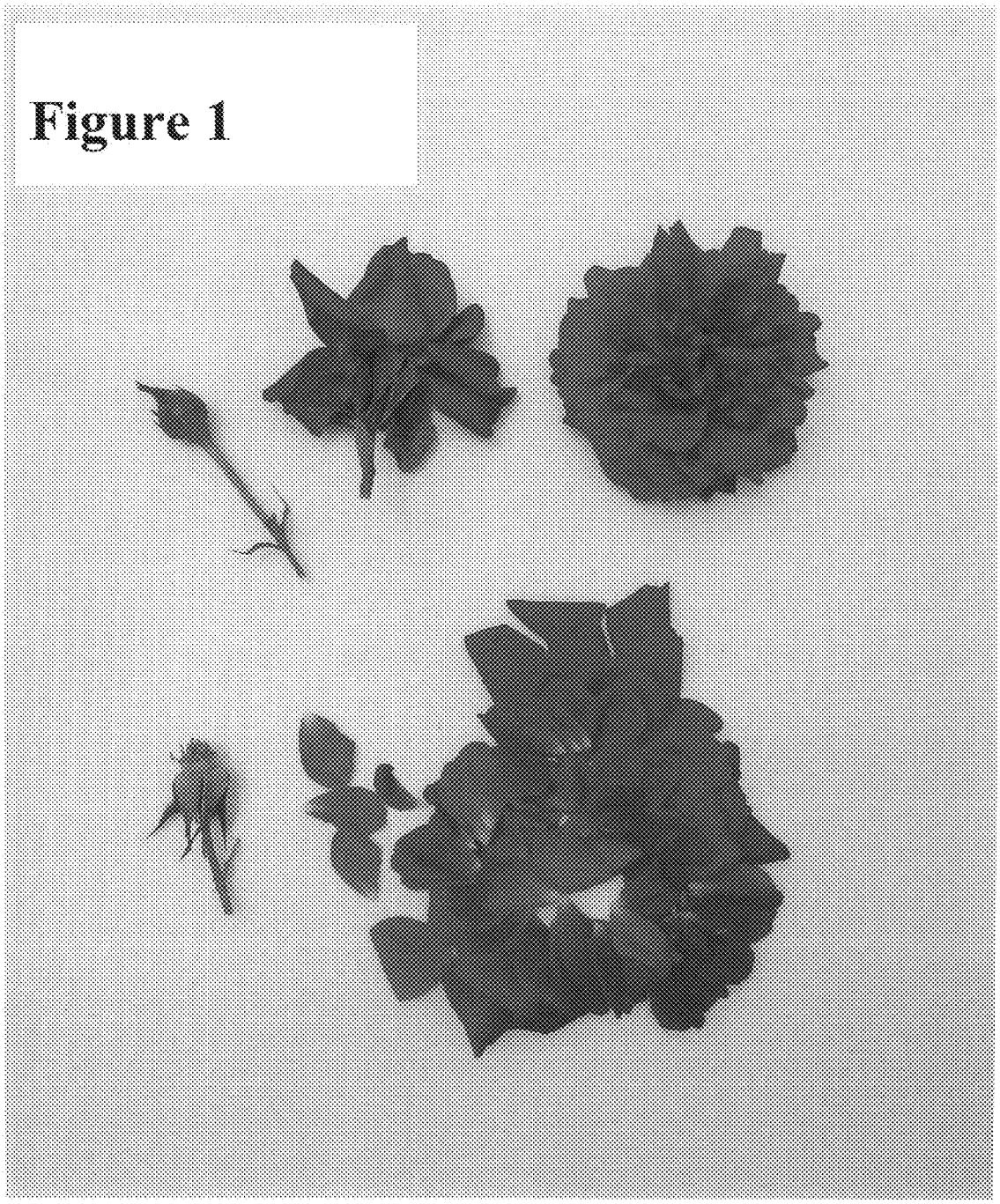
Figure 2:
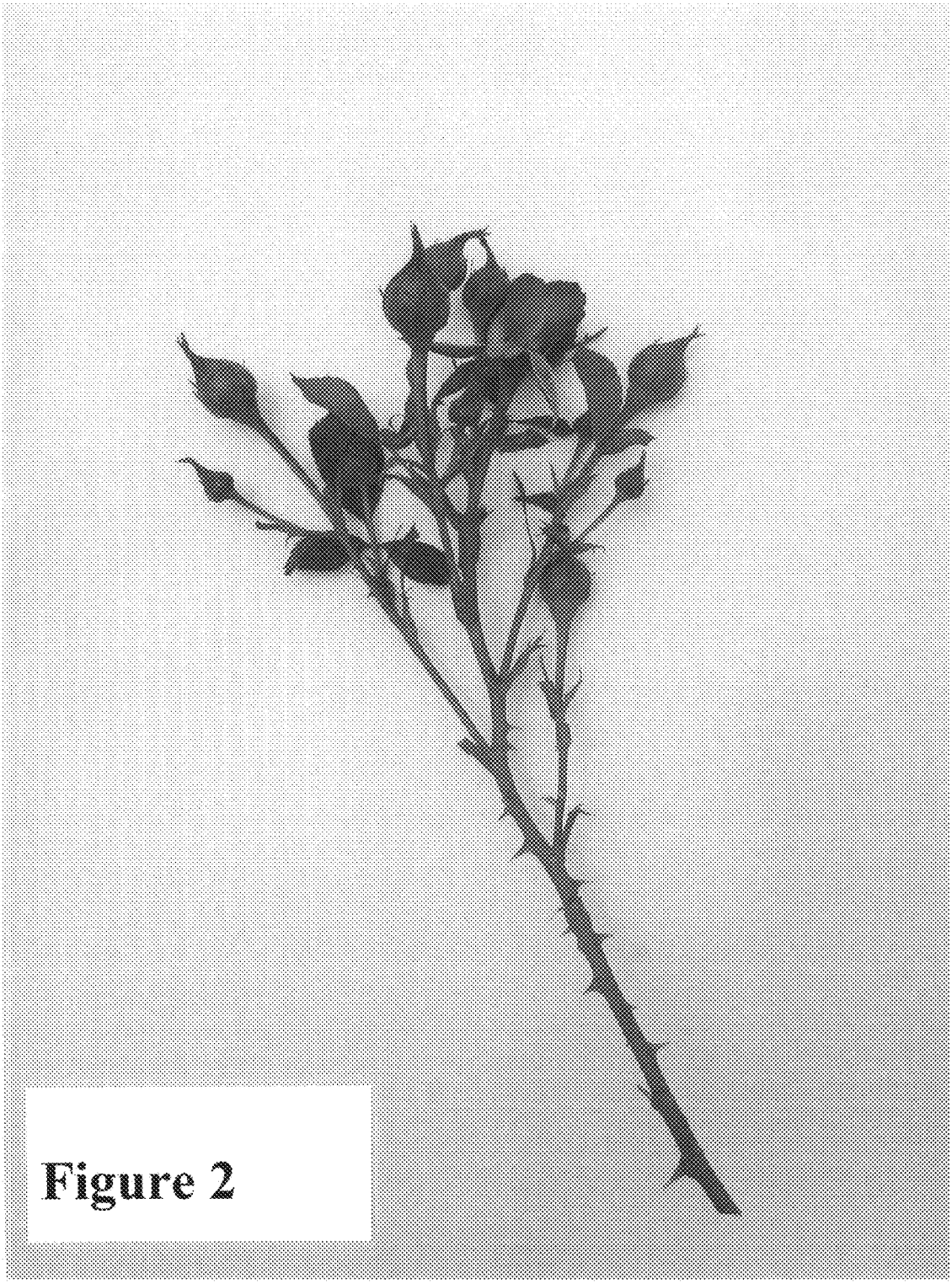
Figure 3:
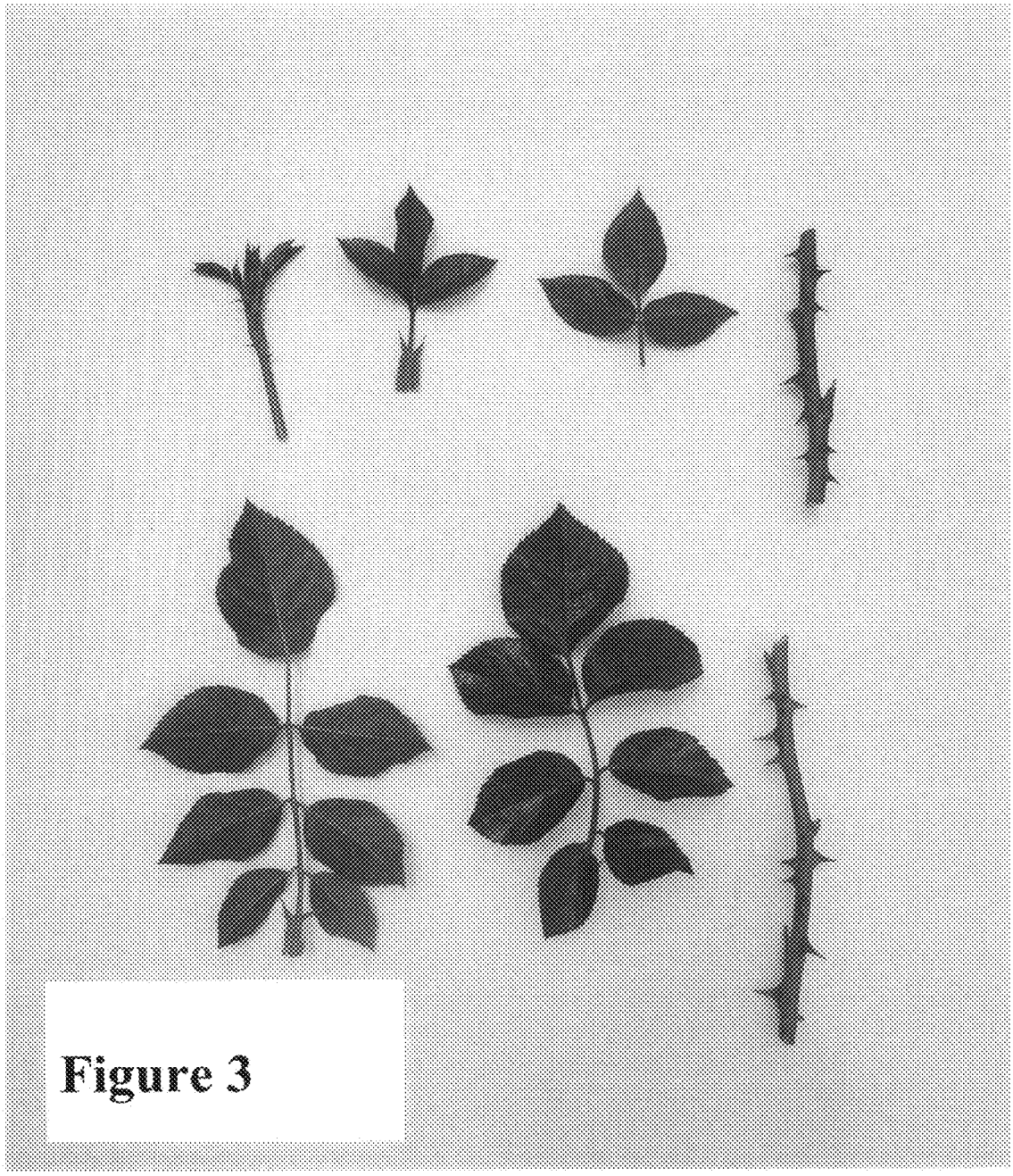

The following is a description of 'Poulcy014', as observed in its growth in in a field nursery Bakersfield, Calif. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulnorm', U.S. Plant Pat. No. 12,552 are compared to 'Poulcy014' in Chart 1.

CHART 1

| | 'Poulcy014' | 'Poulnorm' |
|---|---|---|
| Petal Count | Under normal conditions, flowers have 90 petals total, 7 to 10 of which are petaloids. | 45-50 petals under normal conditions with 4-8 petaloids |
| Bloom habit | continuous | recurrent |
| General Tonality of Flower Color | Red Group 45A | Red Group 34A |

FLOWER AND FLOWER BUD

Blooming habit: Continuous.

Flower bud:

*Size*.—Upon opening, 25 mm in length from base of receptacle to end of bud. Bud diameter is 15 mm.

*Bud form*.—Globose.

*Bud color*.—As sepals divide petals are Red Group 46A.

*Sepal inner surface*.—Color: Green Group 138A. Surface: Smooth.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—25 mm long by 9 mm wide.

*Receptacle*.—Texture: Smooth. Size: 6 mm in height by 9 mm wide. Color: Yellow-Green Group 144A. Anthocyanic pigments the color of Greyed-Purple Group 185A observed. Shape: Funnel shaped.

*Pedicel*.—Surface: Somewhat rough with stipitate glands. Length: 15 to 30 mm. Diameter: 2 to 3 mm. Color: Yellow-Green Group 144B. Anthocyanic pigments the color of Greyed-Purple Group 185A observed. Strength: Moderate.

*Peduncle*.—Length: 20 to 40 mm. Diameter: 2 to 3 mm. Color: Yellow-Green Group 145A.

Flower bud development: Flower buds are borne in clusters of 7 to 15 flower buds per stem, resembling a panicle. Reduced apical dominance in flower habit causes flower buds develop evenly from the base of the plant to the upper branches.

Flower bloom:

*Fragrance*.—Light, old rose scent.

*Duration*.—The blooms have a duration on the plant of approximately 10 to 14 days. Petals fall cleanly away from plant after flowers have fully matured.

*Size*.—Flower diameter is 70 to 80 mm when open. Flower depth is 40 mm.

*Flower shape*.—General shape is a rosette with many slightly overlapping petals of different sizes.

*Shape of flower, side view*.—Upon opening the upper portion is a flattened convex. The lower portion is concave.

Petalage: Under normal conditions, flowers have 90 petals total, 7 to 10 of which are petaloids.

General tonality of flower: Open flowers are Red Group 45A. No changes in tonality observed as the flowers mature.

Petal color:

*Upon opening, outer petals*.—Upper surface: Red Group 45A. Lower surface: Red Group 53C.

*Upon opening, inner petals*.—Upper surface: Red Group 45A. Lower surface: Red Group 53C.

*Basal petal spots, upon opening*.—Upper surface: Yellow Group 2A. Lower surface: Yellow Group 2C.

*After opening, outer petals*.—Upper surface: Red Group 45A. Lower surface: Red Group 53C.

*After opening, inner petals*.—Upper surface: Red Group 45A. Lower surface: Red Group 53C.

*Basal petal spots, after opening*.—Upper surface: Yellow Group 2A. Lower surface: Yellow Group 2C.

Petals:

*Petal reflex*.—Somewhat reflexed.

*Margin*.—Entire and uniform with weak undulations of margin observed.

*Shape*.—Generally narrow elliptic. Apex shape: Rounded. Base shape: Acute.

*Size*.—32 mm (l)×26 mm (w).

*Texture*.—Smooth.

*Thickness*.—Average.

Petaloids:

*Size*.—15 mm (l) by 12 mm (w).

*Quantity*.—7 to 10.

*Shape*.—Asymmetric, with a rounded apex and acute base. Occasionally the apex has a cleft at the center of the margin.

*Color*.—Upper surface is Red Group 45A. Lower Red Group 53C.

Reproductive organs:

*Pollen*.—None observed.

*Anthers*.—Size: 2 mm in length. Color: Yellow Group 13B. Quantity: 38 on average.

*Filaments*.—Color: Yellow Group 1D. Length: 3 mm.

*Pistils*.—Length: 5 mm. Quantity: 40 on average.

*Stigmas*.—Color: Greyed-Yellow Group 162D.

*Styles*.—Color: Yellow-Green Group 145D.

*Location of stigmas*.—Superior in location relative to the length of the filaments and the height of the anthers.

*Hips*.—None Observed.

PLANT

Plant growth: Arching. Plants are 160 cm in height, and 100 cm wide.

Stems:

*Color*.—Juvenile growth: Yellow-Green Group 144A with intonations of Greyed-Red Group 178A. Mature growth: Yellow-Green Group 144B.

*Length*.—Canes are 40 to 100 cm from the base of the plant to the flowering portion.

*Diameter*.—7 mm.

*Internodes*.—On mature canes, there is an average distance of 45 mm between nodes.

*Surface texture*.—Young wood: Smooth. Older wood: Smooth.

Long prickles:

*Incidence*.—12 prickles per 10 cm of stem.

*Size*.—Average length of prickles on mature stems is 8 mm.

*Shape*.—Upper portion is linear. Lower portion is concave.

*Color*.—Juvenile prickles: Greyed-Red Group 181A. Mature prickles: Greyed-Orange Group N170B and Greyed-Red Group 181A.

Plant foliage:

*Compound leaf*.—120 mm (l)×80 (w).

*Quantity*.—2 leaves per 10 cm of stem on average.

*Leaf bearing angle to the stem*.—60 degrees.

*Color of juvenile foliage*.—Upper side: Yellow-Green Group 146A. Lower side: Yellow-Green Group 146B. Anthocyanin: Greyed-Red Group 178A on the upper surface margins, and generalized on the lower surface.

*Color of mature foliage*.—Upper side: Yellow-Green Group 147A. Lower side: Yellow-Green Group 147B.

Plant leaves and leaflets:

*Stipules*.—Size: 15 mm in length and about 8 mm wide. Quantity: 2 per compound leaf. Shape: Linear, slightly broad based with outward extending apices. Margins: Finely serrated with few stipitate glands. Color: Yellow-Green Group 146A.

*Petiole*.—Length: 20 mm. Diameter: 2 mm.

*Upper surface*.—Color: Yellow-Green Group 144A.

*Lower surface*.—Color: Yellow-Green Group 144B. Observations: Small prickles observed.

*Rachis*.—Length: 50 mm. Upper surface: Color: Yellow-Green Group 144A.

*Lower surface*.—Color: Yellow-Green Group 144B. Observations: Small prickles observed.

*Leaflet*.—Quantity: Normal number of leaflets per leaf in the middle of the stem is 7 leaflets. Margins: Serrated. Size: Average size of the terminal leaflet on normal leaves is 45 mm in length by 38 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Climbing rose class named 'Poulcy014', substantially as illustrated and described herein, due to its abundant red flowers, disease resistance, and extended period of bloom.

* * * * *